US012746182B2

(12) United States Patent
Xiong et al.

(10) Patent No.: US 12,746,182 B2
(45) Date of Patent: Sep. 29, 2026

(54) ANTI-LOOSENING FIXING STRUCTURE FOR BOTTOLE BODY OF FLANGEING BOTTLE

(71) Applicant: SUZHOU HEALTHY TREE MEDICAL TECHNOLOGY CO., LTD., Suzhou (CN)

(72) Inventors: Changyan Xiong, Suzhou (CN); Longfeng Dai, Suzhou (CN); Sixian He, Suzhou (CN); Linchuan Yi, Suzhou (CN); Ming Hao, Suzhou (CN); Xingwu Li, Suzhou (CN); Kai Wang, Suzhou (CN)

(73) Assignee: SUZHOU HEALTHY TREE MEDICAL TECHNOLOGY CO., LTD., Suzhou (CN)

( * ) Notice: Subject to any disclaimer, the term of this patent is extended or adjusted under 35 U.S.C. 154(b) by 402 days.

(21) Appl. No.: 18/419,604

(22) Filed: Jan. 23, 2024

(65) Prior Publication Data

US 2024/0198007 A1 Jun. 20, 2024

Related U.S. Application Data

(63) Continuation of application No. PCT/CN2023/095748, filed on May 23, 2023.

(30) Foreign Application Priority Data

Jul. 29, 2022 (CN) ......................... 202221993646.0

(51) Int. Cl.
*A61J 1/06* (2006.01)
*A61M 5/24* (2006.01)

(52) U.S. Cl.
CPC ...... *A61J 1/062* (2013.01); *A61M 2005/2407* (2013.01); *A61M 2005/2418* (2013.01); *A61M 2005/2477* (2013.01)

(58) Field of Classification Search
CPC ............ A61J 1/062; A61M 2005/2407; A61M 2005/2418; A61M 2005/2477
See application file for complete search history.

(56) References Cited

U.S. PATENT DOCUMENTS 9,022,990 B2 * 5/2015 Chevallier ............ A61M 5/326 604/198
9,220,848 B2 * 12/2015 Chevallier ............ A61M 5/326

FOREIGN PATENT DOCUMENTS

CN 110917452 A 3/2020
CN 111888581 A 11/2020

(Continued)

*Primary Examiner* — Bradley J Osinski
(74) *Attorney, Agent, or Firm* — PORUS IP LLC

(57) ABSTRACT

The present disclosure may provide an anti-loosening fixing structure for a bottle body of a flanging bottle. The anti-loosening fixing structure for the bottle body of the flanging bottle may comprise a fixing body, the bottle body being installed in the fixing body, and an upper end of the bottle body being arranged with a flange structure, wherein the top end of the fixing body may be arranged with a limiting ring, the limiting ring may be arranged with side limiting components that are arranged in a mirror distribution, an elastic support structure may be arranged in the storage space of the upper end of the bottle body, the upper end of the fixing body may be arranged with a guiding cycle, the guiding cycle may be arranged with upper end limiting components that are arranged in the mirror distribution.

19 Claims, 15 Drawing Sheets

(56) References Cited

FOREIGN PATENT DOCUMENTS

| | | | |
|---|---|---|---|
| CN | 213609015 | U | 7/2021 |
| CN | 215386587 | U | 1/2022 |
| CN | 218589468 | U | 3/2023 |
| EP | 0413880 | A1 | 2/1991 |

* cited by examiner

ANTI-LOOSENING FIXING STRUCTURE FOR BOTTOLE BODY OF FLANGEING BOTTLE

CROSS-REFERENCE TO RELATED APPLICATIONS

This application is a Continuation of International Application No. PCT/CN2023/095748, filed on May 23, 2023, which claims priority to Chinese Patent Application No. 202221993646.0, filed on Jul. 29, 2022, the contents of which are incorporated herein by reference.

TECHNICAL FIELD

The present disclosure relates to a fixing structure, and in particular to an anti-loosening fixing structure for a bottle body of a flanging bottle.

BACKGROUND

Currently, conventional syringes perform a corresponding fixing by fixing a bottle body for storing the medicament based on a fixing body. However, due to a fit tolerance, the bottle body tends to move up and down or sway from side to side relative to the fixing body when subjected to an external force. In this way, there is a risk that the bottle body may break if the external force is relatively high. If the bottle body is placed relying solely on filling the fit tolerance, an interference fit may be easily occurred during the bonding period, resulting in the bottle body not being placed in place. The prior art uses a fixing claw to fix a fixing flange of a syringe barrel, which can only realize a simple longitudinal restriction of the bottle body, and is unable to carry out a transversal displacement binding. Further, when the fixing flange is clamped in, the fixing claw may be jammed, resulting in the bottle body not being able to be installed smoothly.

It is desirable to provide an anti-loosening fixing structure for a bottle body of a flanging bottle to improve a limiting capacity of the fixing structure.

SUMMARY

One of the embodiments of the present disclosure provides an anti-loosening fixing structure for a bottle body of a flange bottle. The anti-loosening fixing structure for the bottle body of the flange bottle may comprise a fixing body, the bottle body being installed in the fixing body, and an upper end of the bottle body being arranged with a flange structure, wherein the top end of the fixing body may be arranged with a limiting ring, the limiting ring may be arranged with side limiting components that are arranged in a mirror distribution, a storage space of the upper end of the bottle body may be provided between the side limiting components, an clastic support structure may be arranged in the storage space of the upper end of the bottle body, the upper end of the fixing body may be arranged with a guiding cycle, the guiding cycle may be arranged with upper end limiting components that are arranged in the mirror distribution, and the flange structure may be in contact with the upper end limiting components.

BRIEF DESCRIPTION OF THE DRAWINGS

The present disclosure is further illustrated in terms of exemplary embodiments. These exemplary embodiments are described in detail with reference to the drawings. These embodiments are not limited. In these embodiments, the same number represents the same structure, wherein.

DETAILED DESCRIPTION

The following specific embodiments of the present utility model are described in further detail in connection with the accompanying drawings and embodiments. The following embodiments are used to illustrate the present utility model, but are not intended to limit the scope of the present utility model.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term “system,” “engine,” “unit,” “module,” and/or “block” used herein are one method to distinguish different components, elements, parts, section or assembly of different level in ascending order. However, the terms may be displaced by another expression if they achieve the same purpose.

The terminology used herein is for the purpose of describing particular example embodiments only and is not intended to be limiting. As used herein, the singular forms “a,” “an,” and “the” may be intended to include the plural forms as well, unless the context clearly indicates otherwise. It will be further understood that the terms “comprise,” “comprises,” and/or “comprising,” “include,” “includes,” and/or “including,” when used in this specification, specify the presence of stated features, integers, steps, operations, elements, and/or components, but do not preclude the presence or addition of one or more other features, integers, steps, operations, elements, components, and/or groups thereof.

Figure 1:
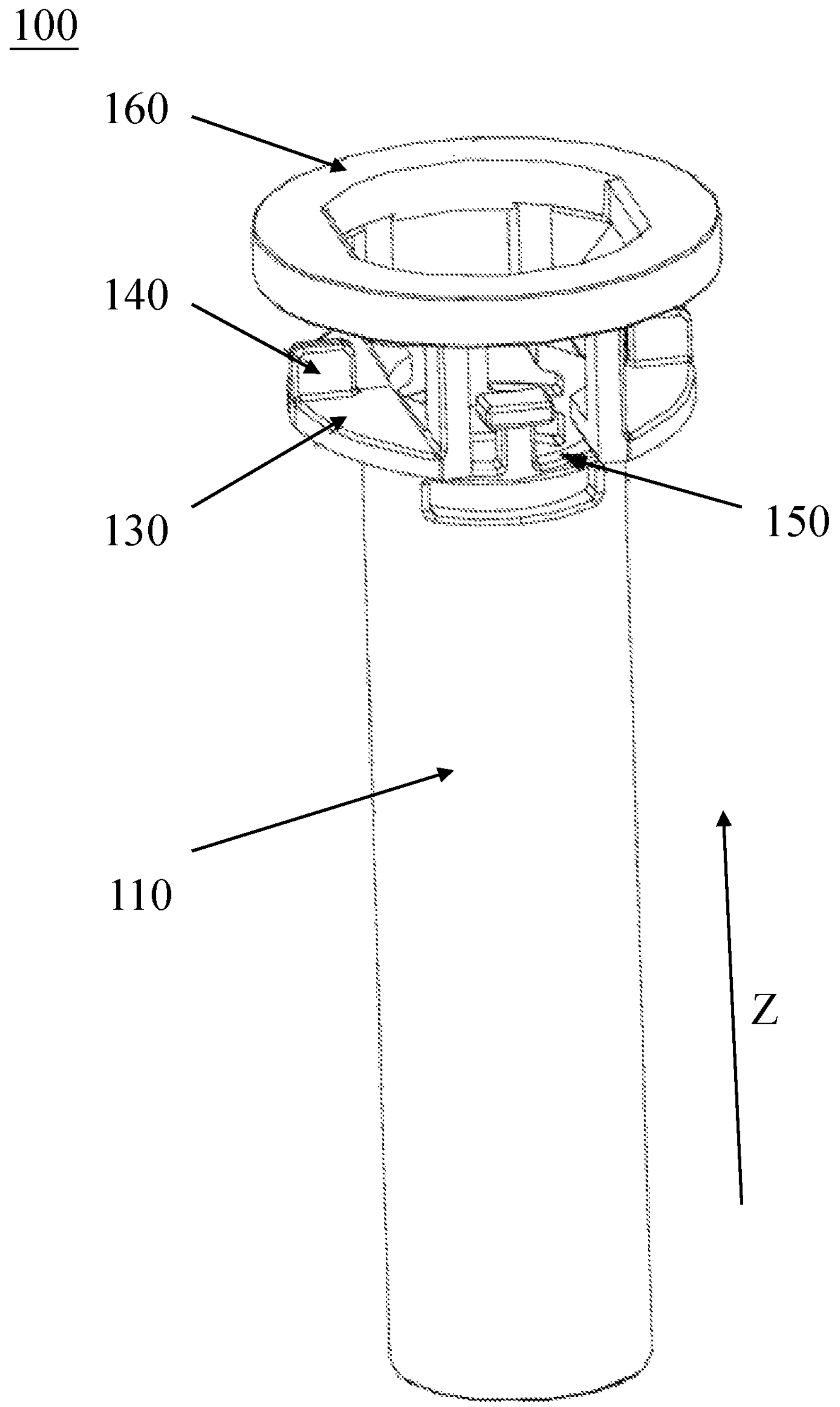
FIG. 1 is a schematic diagram illustrating an exemplary structure of a fixing body according to some embodiments of the present disclosure.
Figure 2:
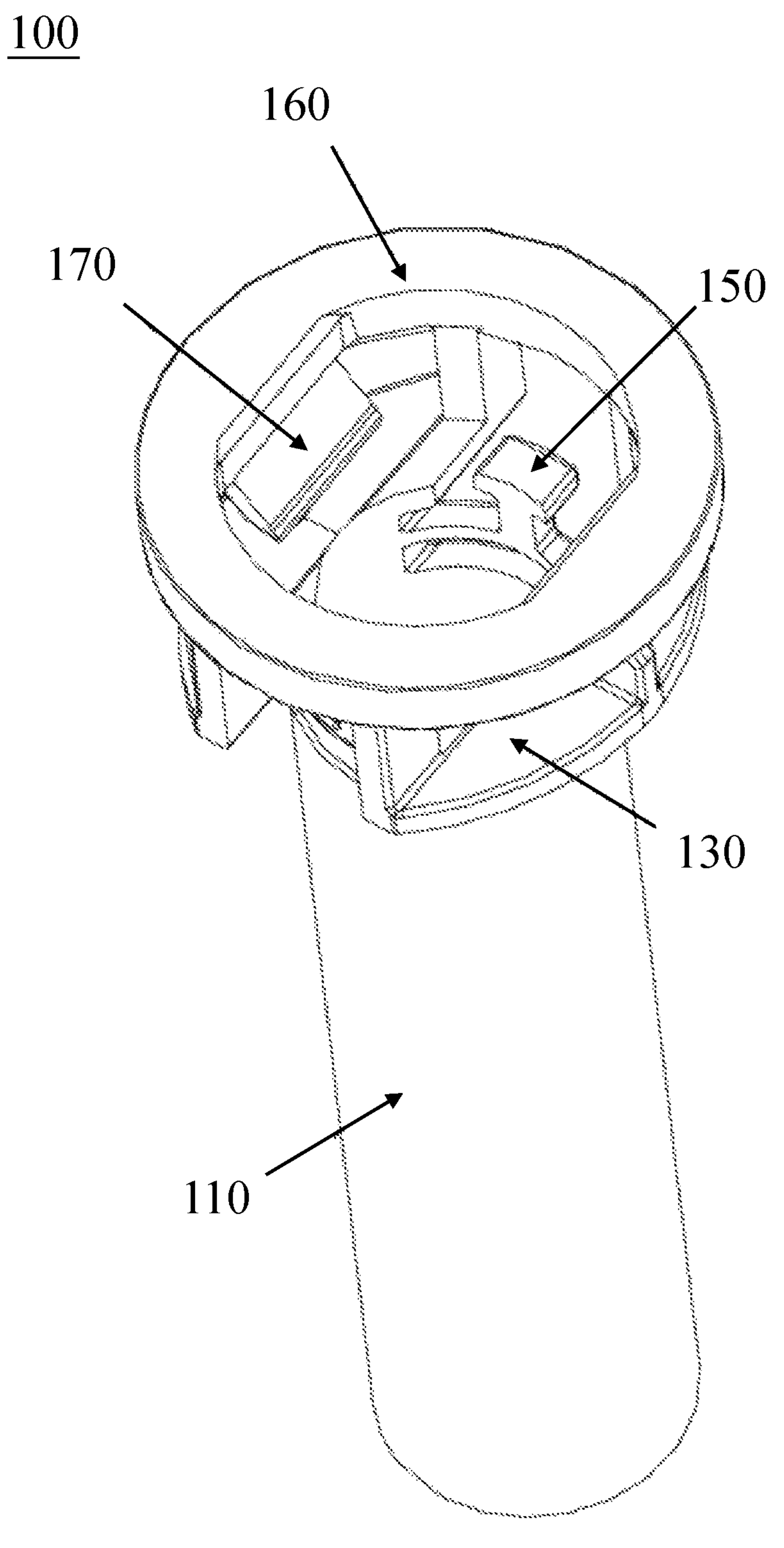
FIG. 2 is a schematic diagram illustrating an exemplary distribution structure of an upper end limiting component according to some embodiments of the present disclosure.
Figure 3:
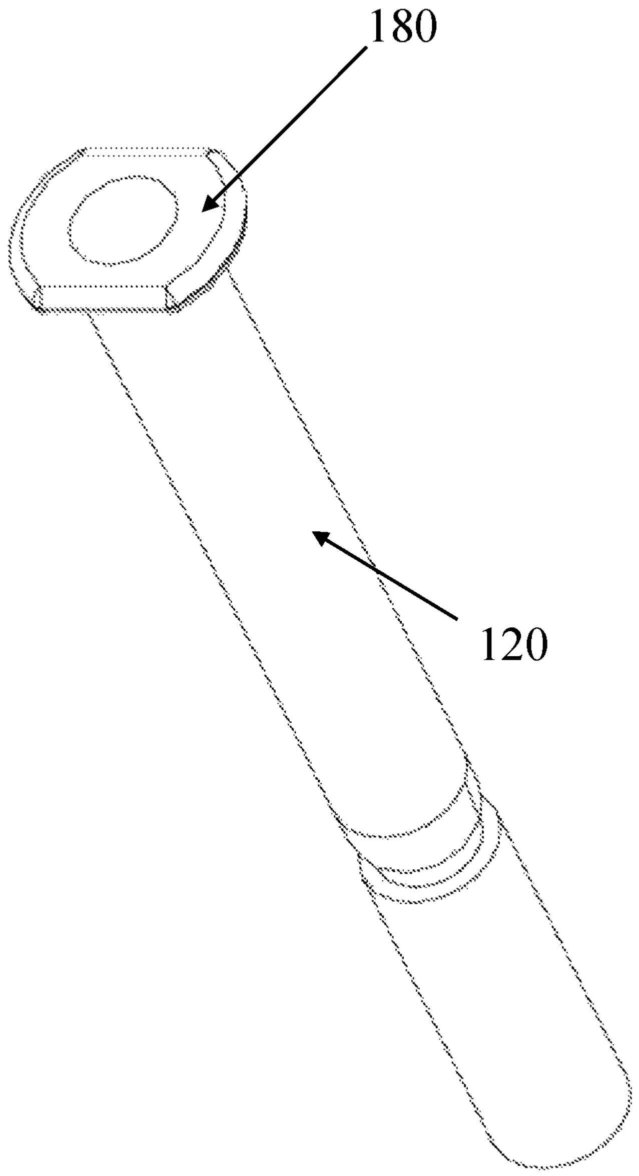
FIG. 3 is a schematic diagram illustrating an exemplary structure of a bottle body with a notched flange according to some embodiments of the present disclosure.
Figure 4:
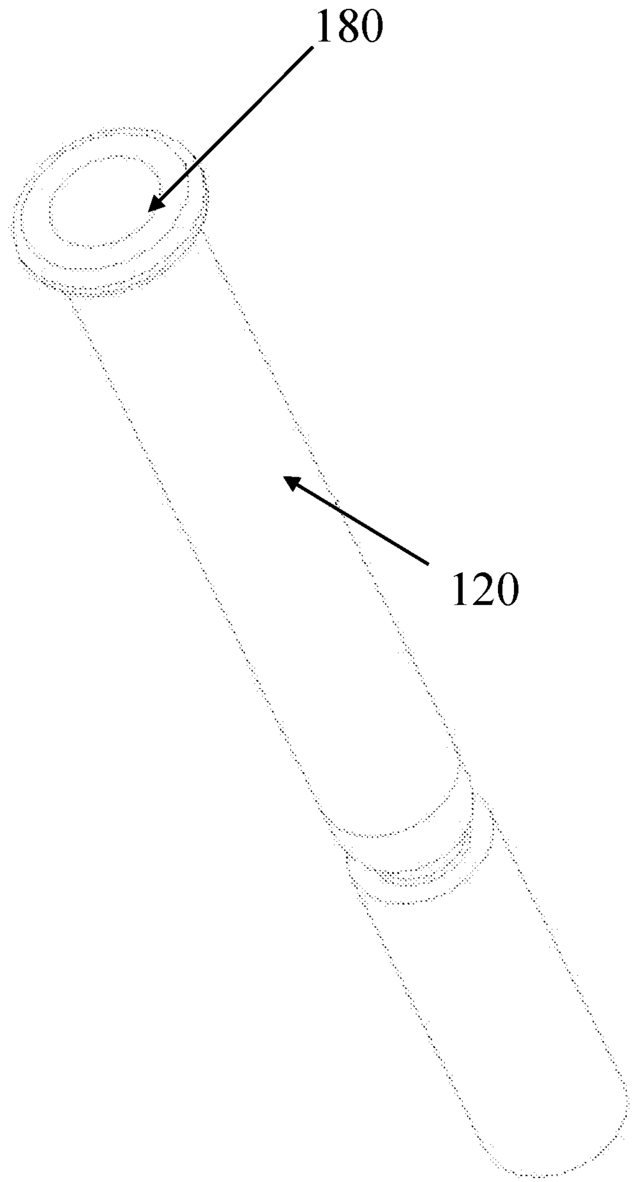
FIG. 4 is a schematic diagram illustrating an exemplary structure of a bottle body with a circular flange shown according to some embodiments of the present disclosure.
Figure 5:
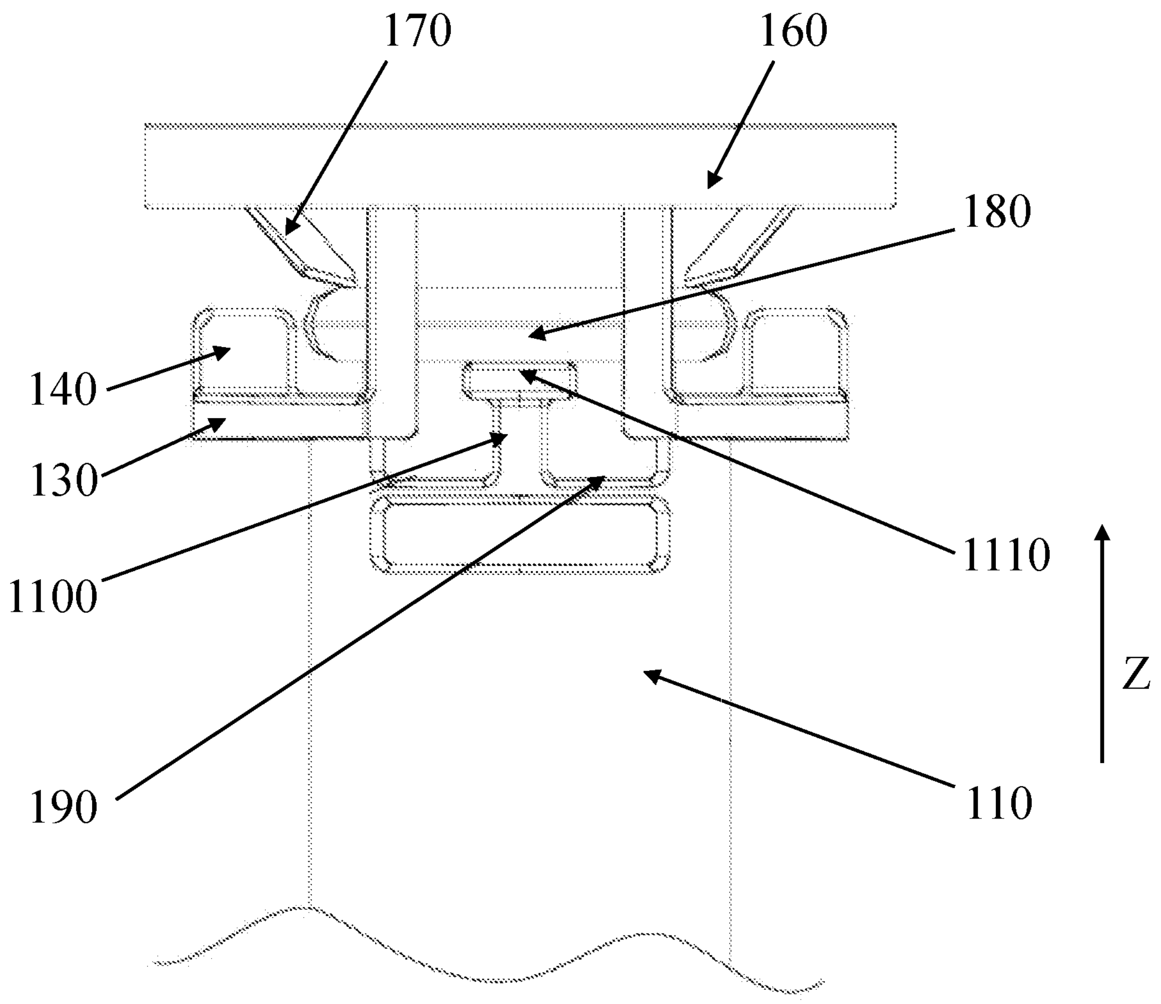
FIG. 5 is a schematic diagram illustrating an exemplary combination of a bottle body and a fixing body according to some embodiments of the present disclosure.

FIG. 1 is a schematic diagram illustrating an exemplary structure of a fixing body according to some embodiments of the present disclosure. FIG. 2 is a schematic diagram illustrating an exemplary distribution structure of an upper end limiting component according to some embodiments of the present disclosure. FIG. 3 is a schematic diagram illustrating an exemplary structure of a bottle body with a notched flange according to some embodiments of the present disclosure. FIG. 4 is a schematic diagram illustrating an exemplary structure of a bottle body with a circular flange shown according to some embodiments of the present disclosure. FIG. 5 is a schematic diagram illustrating an exemplary combination of a bottle body and a fixing body according to some embodiments of the present disclosure.

In some embodiments, as shown in FIGS. 1-5, the anti-loosening fixing structure for the bottle body of the flanging bottle 100 may include a fixing body 110, a bottle body 120 may be installed in the fixing body 110, and an upper end of the bottle body 120 may be arranged with a flange structure 180. The top end of the fixing body 110 may be arranged with a limiting ring 130, and the limiting ring 130 may be arranged with side limiting components 140 that are arranged in a mirror distribution. A storage space of the upper end of the bottle body 120 may be provided between the side limiting components 140, an elastic support structure 150 may be arranged in the storage space of the upper end of the bottle body 120, the upper end of the fixing body 110 may be arranged with a guiding cycle 160, the guiding cycle 170 may be arranged with upper and limiting components 170 that are arranged in the mirror distribution, and the flange structure 180 may be in contact with the upper end limiting components 170.

The fixing body 110 refers to a main structure of the anti-loosening fixing structure. In some embodiments, the fixing body 110 may be a cylindrical structure. In some embodiments, the fixing body 110 may be provided with a cavity internally, and the bottle body 120 may be installed within the cavity. In some embodiments, the cavity may be cylindrical. In some embodiments, the cavity may be coaxial with the fixing body 110.

The flange structure 180 refers to a connecting structure extending radially outward along the bottle body 120 and may be connected with other structures (e.g., a flange plate, etc.). In some embodiments, the flange structure 180 may be arranged on an outer side of the bottle body 120 in an annular shape. In some embodiments, the flange structure 180 may be arranged on at least one end of the bottle body 120.

In some embodiments, the top end of the fixing body 110 may be arranged with a limiting ring 130, the limiting ring 130 may be arranged with side limiting components 140 that are arranged in a mirror distribution, and a storage space of the upper end of the bottle body 120 may be provided between the side limiting components 140.

The limiting ring 130 may be configured to limit a movement of the flange structure 180 along an axial direction of the fixing body 110. In some embodiments, the limiting ring 130 may be a circular structure, and the limiting ring 130 may be coaxial with the fixing body 110.

The storage space may be configured for installing an upper end of the bottle body 120, such as the flange structure 180. The side limiting component 140 may be configured to effectively limit a side of the upper end of the bottle body 120 (e.g., a side of the flange structure 180) to avoid non-essential traverse of the upper end of the bottle body 120, such as a movement along a radial direction of the limiting ring 130. In some embodiments, a count of the side limiting components 140 may be two. In some embodiments, the side limiting component 140 may be butted with the upper end of the bottle body 120. In some embodiments, the side limiting components 140 may be an elastic structure, and the side limiting component 140 may be elastically connected with the upper end of the bottle body 120.

In some embodiments, each of the side limiting components 140 may be an elastic block. In some embodiments, each of the side limiting components may be a rectangular sheet, a top of the rectangular sheet may be arranged with an arc chamfer. By providing the arc chamfer, hands of a user may not be scratched during manual assembly, and non-essential interference with other components may not be caused during assembly and use.

In some embodiments, an elastic support structure 150 may be arranged at an upper end of the fixing body 110 (e.g., an end facing up along a Z-direction in FIG. 1).

The elastic support structure 150 may be capable of being used to provide a support to other structures (e.g., the flange structure 180). In some embodiments, at least a portion of the clastic support structure 150 may be located at an upper end of the storage space. For example, the at least a portion of the elastic support structure 150 may be located above the storage space along the Z-direction of FIG. 1 from below to top. The elastic support structure 150 can achieve a proper lifting of the upper end of the bottle body 120 (e.g., the flange structure 180) to satisfy a limiting of a bottom of the upper end of the bottle body 120 (e.g., a lower surface of the flange structure 180). In some embodiments, the elastic support structure 150 may form an elastic connection with the flange structure 180. By filling the bottle body 120 into the cavity of the fixing body 110, the clastic support structure 150 can play a role of buffering and vibration reduction and prevent the flange structure 180 from crashing In some embodiments, the elastic support structure 150 may be an clastic support arm. During assembly, even if the upper end of the bottle body 120 is pressed excessively, the elastic support structure can give effective rebound support, which can prevent the bottle body 120 from overextending into the fixing body 110 and lead to jamming. In some embodiments, the clastic support arm may include an clastic cross-piece 190 connecting with the fixing body 110, the elastic cross-piece 190 may be vertically arranged with an arm body 1100, and an upper end of the arm body 1100 is arranged with a support block 1110.

The clastic cross-piece 190 may be capable of being used as an installing base for installing the arm body 1100. In some embodiments, the clastic cross-piece 190 may be connected with the fixing body 110. In some embodiments, the elastic cross-piece 190 may be connected with the fixing body 110 through variety connection manner such as a bonding or screw rod connection.

The arm body 1100 may be capable of being used as an installing base for installing the support block 1110. The arm body 1100 may be capable of transmitting a pressure to the clastic cross-piece 190. In some embodiments, an area of the clastic cross-piece 190 along an axial direction of the fixing body 110 may be greater than an area of the arm body 1100 along the axial direction of the fixing body 110, the elastic cross-piece 190 may spread the pressure transmitted by the arm body 1100.

The support block 1110 may be configured to support an upper end of the bottle body 120 (e.g., the flange structure 180). When installing the bottle body 120, the bottle body 120 may transmit the pressure to the support block 1110, ultimately allowing the pressure to be dispersed through the clastic cross-piece 190. In some embodiments, the area of the support block 1110 along the axial direction of the fixing body 110 may be larger than the area of the arm body 1100 along the axial direction of the fixing body 110, which can increase a contact area between the support block 1110 and the bottle body 120 and improve a stability of the support block 1110 in supporting the bottle body 120.

In some embodiments, the clastic cross-piece 190, the arm body 1100, and the support block 1110 may be integrally molded. In some embodiments, the elastic support arm may be integrally molded with the fixing body 110.

When the bottle body 120 is subjected to a downward stress, the stress may be released by the deformation of the elastic cross-piece 190, while the elastic cross-piece can achieve a moderate rebound to give a better support to the bottle body 120.

The guiding cycle 160 may be capable of restricting a movement direction of the bottle body 120 and may be used for guiding. When installing the bottle body 120, the guiding cycle may guide the bottle body 120 into the cavity of the fixing body 110, which is conducive to improving a precision and efficiency of the installation of the bottle body 120 and reducing the collision of the bottle body 120 during the installation process. In some embodiments, the guiding cycle 160 may be a circular structure. In some embodiments, the guiding cycle 160 may be coaxial with the fixing body 110. In some embodiments, an inner diameter of the guiding cycle 160 may be greater than or equal to a diameter of the flange structure 180.

The upper end limiting component 170 may be configured to restrict a top of the upper end of the bottle body 120 (e.g., an upper surface of the flange structure 180). In some embodiments, the upper end limiting component 170 may be an elastic structure. In some embodiments, the upper end limiting component 170 may be in clastic contact with the top of the upper end of the bottle body 120.

In some embodiments, after the bottle body 120 is placed in place, an upper end of the bottle body 120 may be simultaneously subjected to a three-way clamping limiting by the side limiting component 140, the elastic support structure 150, and the upper end limiting component 170 without loosening.

In some embodiments, the upper end limiting component 170 may be an oblique limiting valve, i.e., the upper end limiting component 170 may tilt inward toward an axis of the guiding cycle 160. The oblique limiting valve may be arranged at a bottom of the oblique slope. By providing the oblique limiting valve, the oblique limiting valve may undergo an appropriate elastic deformation when the bottle body 120 passes through the oblique limiting valve, causing the oblique limiting valve to be squeezed to both sides. After the bottle body 120 has fully entered the fixing body 110, the oblique limiting valve may be reset. The oblique slope may be located on a top of the upper end of the bottle body 120, e.g., the upper surface of the flange structure 180, to provide an effective limiting on the top of the upper end of the bottle body 120. In some embodiments, the oblique slope may be butted with the bottle body 120. By using the upper end limiting component 170, it is possible to longitudinally limit the bottle body 120 timely once the bottle body 120 is placed in place.

In some embodiments, the flange structure 180 may include a circular flange or a notched flange, taking into account different bottle body 120 limiting needs.

The circular flange refers to a flange with a cylindrical side.

The notched flange refers to a flange in which a side of the flange include at least one plane. In some embodiments, the side of the notched flange may include two planes, and the two planes may be mirror symmetrical about a plane passing through a flange axis.

Better limiting can be achieved by using the circular flange or the notched flange to match with the side limiting component 140, the clastic support structure 150, and the upper end limiting component 170. During the assembly, the bottle body 120 of the circular flange does not need to pay attention to a surrounding direction of the bottle body 120. and it is sufficient to satisfy that a straight edge of bottle body 120 of notched flange is parallel to the elastic support structure 150. In some embodiments, the flange structure 180 may also be semi-circular, hexagonal, and other configurations, and as long as the shape of the flange configuration is larger than an opening of the container at the upper end is suitable for the utility model, which may not be repeated herein. At the same time, a suitable limiting ring configuration may be selected according to the corresponding shape of the flange structure 180.

An operation principle of some embodiments of the present invention is as follows:

The bottle body 120 is inserted into the fixing body 110, a stress is applied to the bottle body 120, and the upper end limiting component 170 may deform after being subjected to the stress, and the upper end limiting component 170 may close in toward the two sides of the guiding cycle 160 to form a space. Accompanying the application of the stress to the bottle body 120, the flange structure 180 may pass through the space and then contact the elastic support structure 150. At the moment of contact, the elastic support structure 150 may deform due to the stress and reset back immediately, restricting the flange structure 180 from moving further forward. Finally, the upper end limiting component 170 and the elastic support structure 150 may limit the upper and lower of the flange structure 180, thereby ensuring that the entire bottle body 120 does not shake up and down. At the same time, relying on a lateral limiting of the side limiting component 140, there is also no lateral swaying.

Combine with the above descriptions and the figures, the beneficial effects in the embodiments of the present discourse may include but are not limited to the followings:

1. Based on the three-way clamping limiting by the side limiting component, the elastic support structure, and the upper end limiting component, a solid combination of the bottle body and the fixing body can be ensured without loosening.

2. The upper end limiting component may guide the flange structure move forward and limit the flange structure while it is in the proper position, satisfying an irreversible guiding limiting and ensuring that the bottle body cannot be loosened from the fixing body.

3. By setting an independent elastic support structure, the assembly stress absorption may be satisfied while an effective downward limiting can be realized, which can realize a solid bottom support for the flange structure.

4, the overall structure is simple, which can be transformed to replace the existing fixing body and adapted to the current various types of conventional syringe construction, resulting in a relatively great universality.

Figure 6:
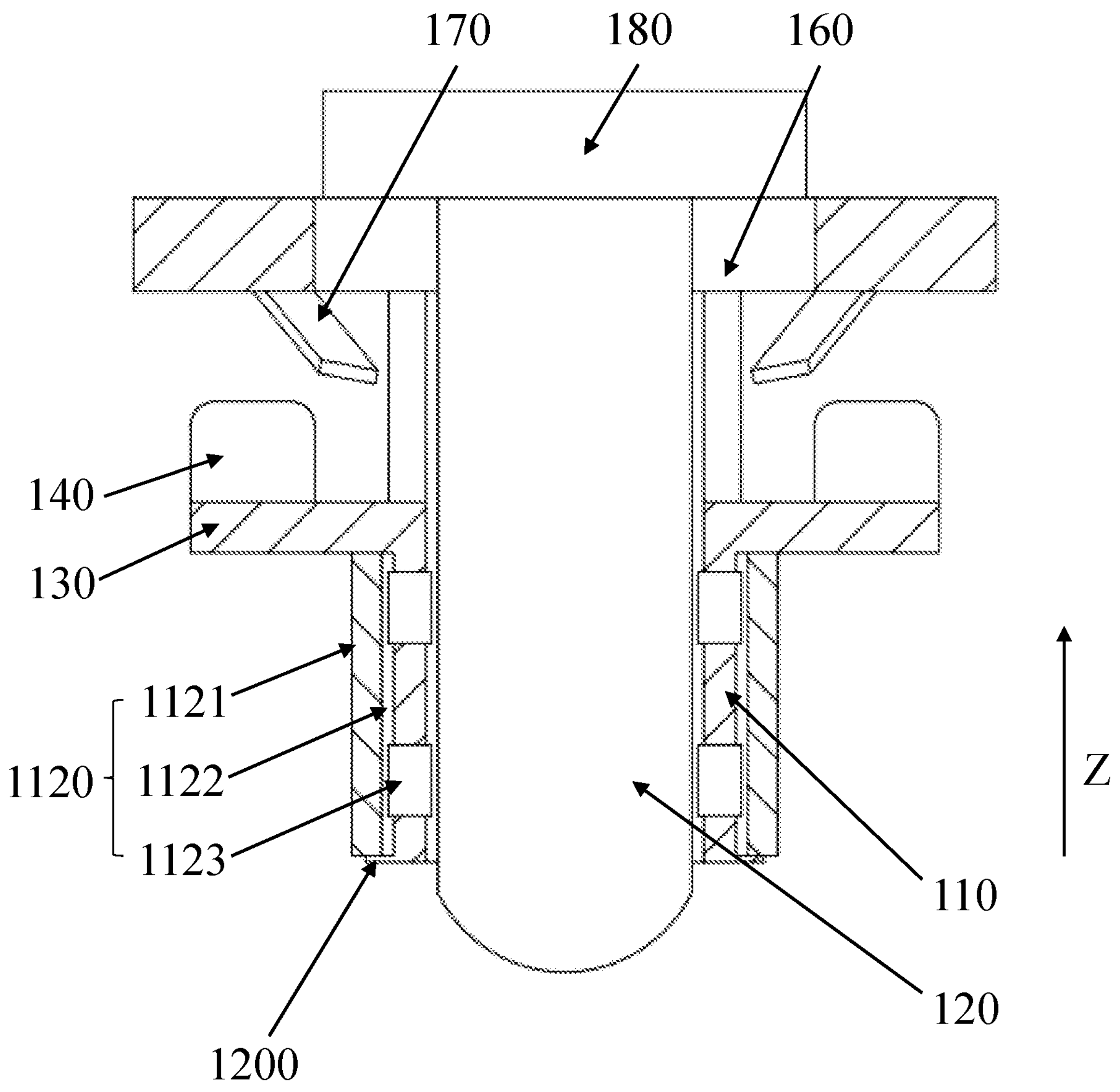
FIG. 6 is schematic diagram illustrating an exemplary reversible limiting structure according to some embodiments of the present disclosure.
Figure 7:
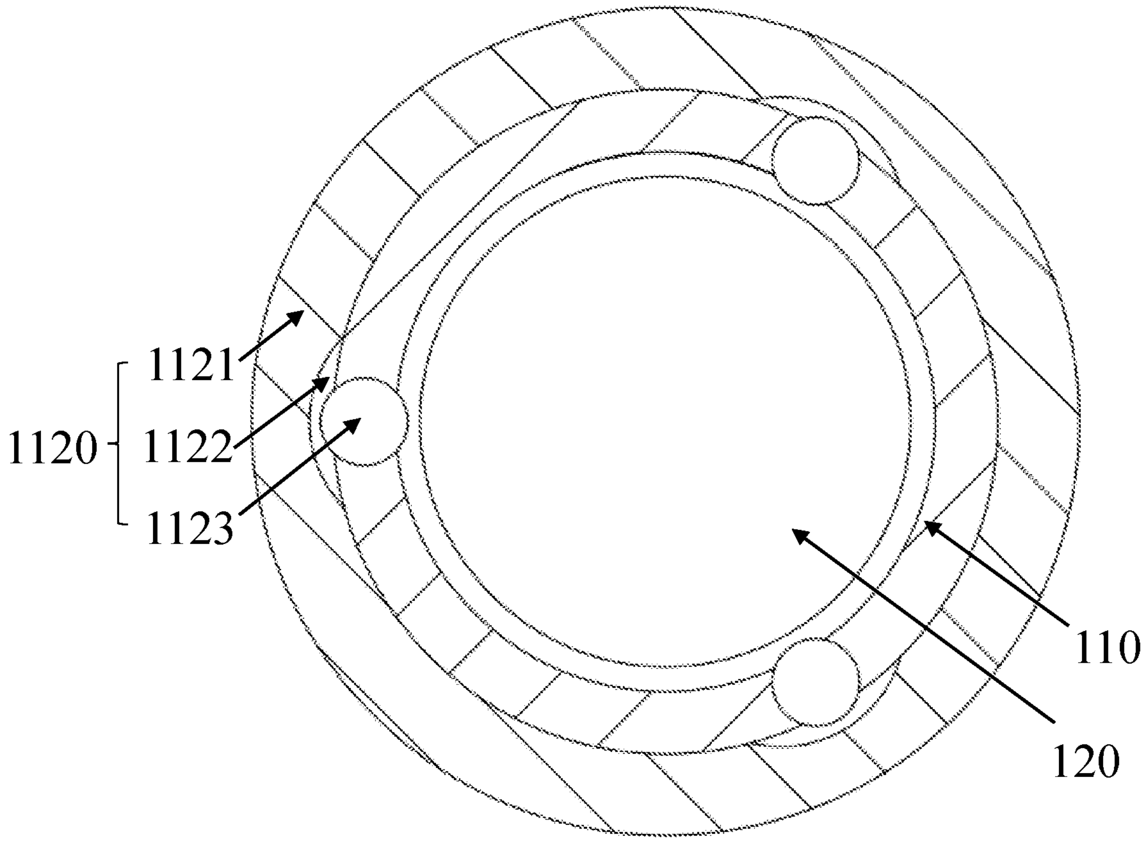
FIG. 7 is a schematic diagram illustrating an exemplary reversible limiting structure in an unlimiting state according to some embodiments of the present disclosure.
Figure 8:
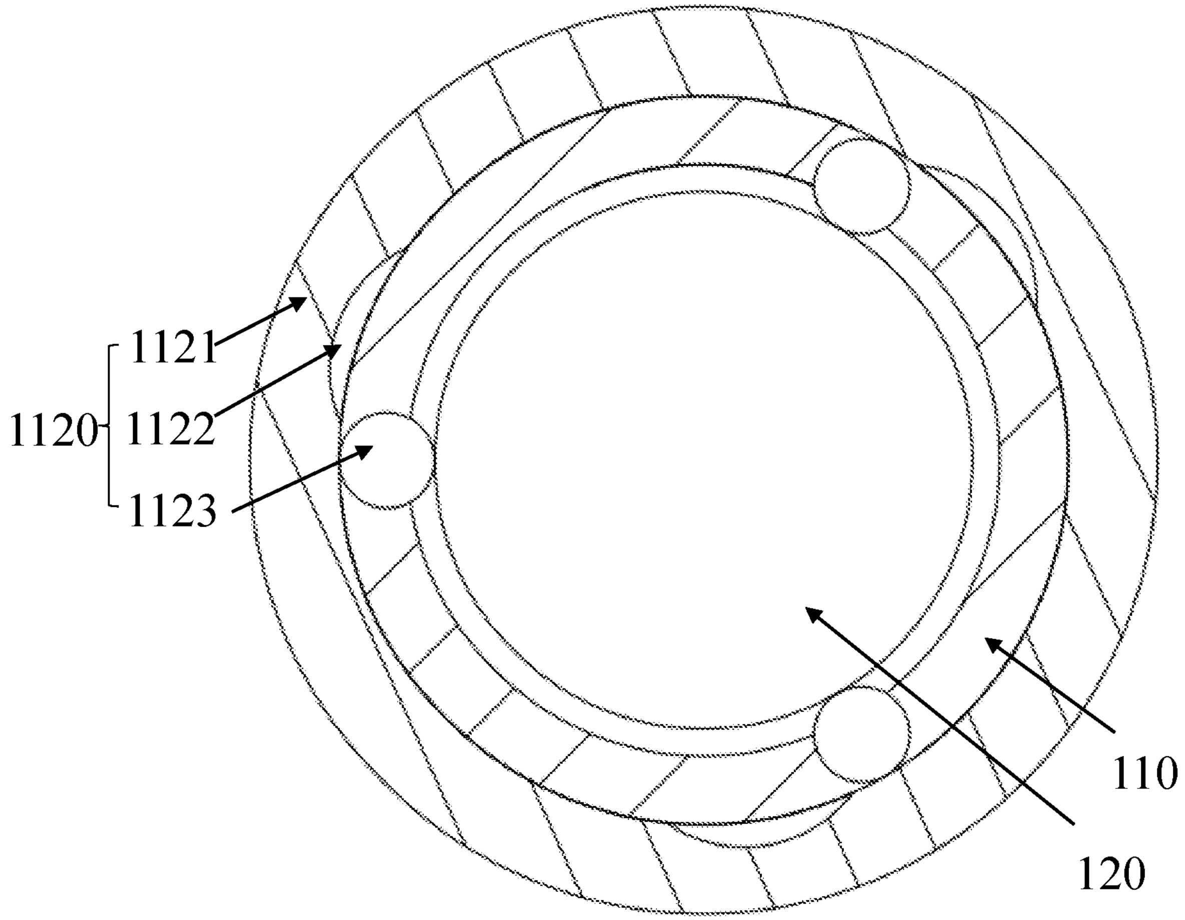
FIG. 8 is a schematic diagram illustrating an exemplary reversible limiting structure in a limiting state according to some embodiments of the present disclosure.

FIG. 6 is schematic diagram illustrating an exemplary reversible limiting structure according to some embodiments of the present disclosure. FIG. 7 is a schematic diagram illustrating an exemplary reversible limiting structure in an unlimiting state according to some embodiments of the present disclosure. FIG. 8 is a schematic diagram illustrating an exemplary reversible limiting structure in a limiting state according to some embodiments of the present disclosure.

In some embodiments, as shown in FIG. 6, FIG. 7, and FIG. 8, a reversible limiting structure 1120 is arranged at a lower end of the fixing body 110 (e.g., along a downward end opposite to the Z direction in FIG. 6).

The reversible limiting structure 1120 refers to a structure that is capable of switching between a limiting state and a unlimiting state. For example, in the limiting state, the reversible limiting structure 1120 may limit the bottle body 120 within the fixing body 110. In the unlimiting state, the reversible limiting structure 1120 may release a limitation of the bottle body 120. In some embodiments, the reversible limiting structure 1120 may include a sleeve 1121 and a roller 1123.

The sleeve 1121 is a cylindrical structure. In some embodiments, the sleeve 1121 may be arranged on an outer side of the lower end of the fixing body 110. In some embodiments, an inner surface of the sleeve 1121 is cylindrical. In some embodiments, the inner surface of the sleeve 1121 may be loosely fitted or snugly affixed to the outer side of the fixing body 110, allowing the sleeve 1121 and the fixing body 110 to rotate relative to each other. In some embodiments, an inner side of the sleeve 1122 may be arranged with one or more cavities with varying cross-section (e.g., on the inner surface of the sleeve 1121).

The cavity with varying cross-section 1122 refers to cavities arranged on the inner surface of the sleeve 1121, and a distance between the cavity and an axis of the sleeve 1121 may gradually vary along a circumferential direction of the sleeve 1121. For example, the distance may gradually increase to a certain set value and then gradually decrease. In some embodiments, the distance between the cavity with varying cross-section 1122 and the axis of the sleeve 1121 may gradually decrease from a middle of the cavity with varying cross-section 1122 along the circumference of the sleeve 1121 to both sides.

The roller 1123 refers to a rolling body that may be rotated relative to other structures (e.g., the fixing body, etc.). In some embodiments, the roller 1123 may be arranged on the fixing body 110, and the roller 1123 may be located between the fixing body 110 and the sleeve 1121. In some embodiments, at least portion of the roller 1123 may be arranged within the cavity with varying cross-section 1122. In some embodiments, the roller 1123 may be a cylindrical roller and/or a spherical roller. In some embodiments, an axis of the cylindrical roller may be parallel to the axis of the fixing body 110. In some embodiments, along a radial direction of the fixing body 110, a maximum dimension of the roller 1123 (e.g., a diameter of the cylindrical roller, a diameter of the spherical roller, etc.) may be greater than a thickness of the fixing body 110. In some embodiments, the roller 1123 may be rotatably connected with the fixing body 110 along the radial direction of the fixing body 110.

In some embodiments, as shown in FIG. 7, when the reversible limiting structure 1120 is in a unlimiting state, at least a portion of the roller 1123 (e.g., a portion near the cavity with varying cross-section 1122) may be inside the cavity with varying cross-section 1122, and the at least a portion of the roller 1123 (e.g., a portion near the cavity of the fixing body 110) may be located inside the fixing body 110 without contacting the bottle body 120. In some embodiments, as shown in FIG. 8, when the reversible limiting structure 1120 is in a limiting state, at least a portion of the roller 1123 (e.g., the portion near the cavity of the fixing body 110) may be located inside the fixing body 110 with contacting the bottle body 120. In some embodiments, a relative rotation of the fixing body 110 and the sleeve 1121 enables the reversible limiting structure 1120 to switch between the unlimiting state and the limiting state. The switching may occur during the relative rotation of the cavity with varying cross-section 1122 and the fixing body 110. During the rotation, the cavity with varying cross-section 1122 may squeeze the roller 1123, causing the roller 1123 to gradually move away from the cavity with varying cross-section 1122 along the radial direction of the fixing body 110 until the roller 1123 and the cavity with varying cross-section 1122 are misaligned. The squeezed roller 1123 may move inward until contacting the bottle body 120, thereby allowing the bottle body 120 to be squeezed and limited.

By using the reversible limiting structure, a portion of the bottle body that extends into an interior of the fixing body can be limited, thereby enhancing an anti-loosening effect of the anti-loosening fixing structure and expanding the applicability to bottle body with or without the flange structure. The reversible limiting structure may also be disassembled, allowing for reusability and increasing the rate of reuse.

In some embodiments, along the axial direction of the fixing body 110 (e.g., the Z-direction in FIG. 1), a projection of the cavity with varying cross-section 1122 may include a plurality of oblique lines and/or at least one arc. In some embodiments, the arc may be a circular arc. In some embodiments, the cavity with varying cross-section 1122 may be enclosed by two sides. For example, one side of the cavity with varying cross-section 1122 may be an outer side of the fixing body 110, and the other side may be an approximate arc-shaped surface formed by a plurality of planes. As another example, one side of the cavity with varying cross-section 1122 may be an outer side of the fixing body 110, and the other side may be an approximate arc-shaped surface formed by a plurality of planes and at least one arc. As another example, one side of the cavity with varying cross-section 1122 may be an outer side of the fixing body 110, and the other side may be an arc-shaped surface.

By making the projection of the cavity with varying cross-section 1122 oblique line and/or arc, the machining of varying cross-section may be more convenient, and the roller rolling in the varying cross-section may be more smooth.

In some embodiments, at least one the roller 1123 and the cavity with varying cross-section 1122 may be provided separately. In some embodiments, a plurality of cavities with varying cross-section 1122 and rollers 1123 may be provided separately, such as 3, 4, or etc. In some embodiments, a plurality of cavities with varying cross-section 1122 and rollers 1123 may be provided separately, and a cavity with varying cross-section 1122 and a roller 1123 inside the cavity with varying cross-section 1122 may be set as a group, correspondingly. As shown in FIGS. 7 and 8, three groups of the rollers 1123 and the cavities with varying cross-section 1122 may be provided. The multiple groups of the rollers 1123 and the cavities with varying cross-section 1122 may also be provided, such as 6 groups, 8 groups, or the like, to achieve a more solid fixation.

In some embodiments, the cavities with varying cross-section may be distributed around the axis of the fixing body 110. In some embodiments, the cavities with varying cross-section may be evenly distributed in a circular pattern around the axis of the fixing body 110.

By setting a plurality of cavities with varying cross-section and rollers, it is possible to use the multiple rollers to squeeze the bottle body simultaneously, thereby enhancing the effect of the rollers on limiting the bottle body. The cavities with varying cross-section distributed around the axis of the fixing body enable the rollers to exert extrusion and limitation on the bottle body from multiple angles, which is advantageous for improving the stability of the bottle body, resulting in improving a coaxiality between the bottle body and the fixing body, preventing the bottle body from tilting and colliding with the fixing body, and protecting the bottle body from damage.

In some embodiments, the roller 1123 is made of an elastic material, such as rubber, silicone, plastic, or the like. In some embodiments, the roller 1123 may be in clastic contact with the bottle body 120.

when squeezing the bottle body with the roller, the use of the roller made up with the clastic material can prevent the bottle body from being crushed. Additionally, the rollers can undergo elastic deformation, thereby enhancing the effect of squeezing and restricting the bottle body.

Figure 9:
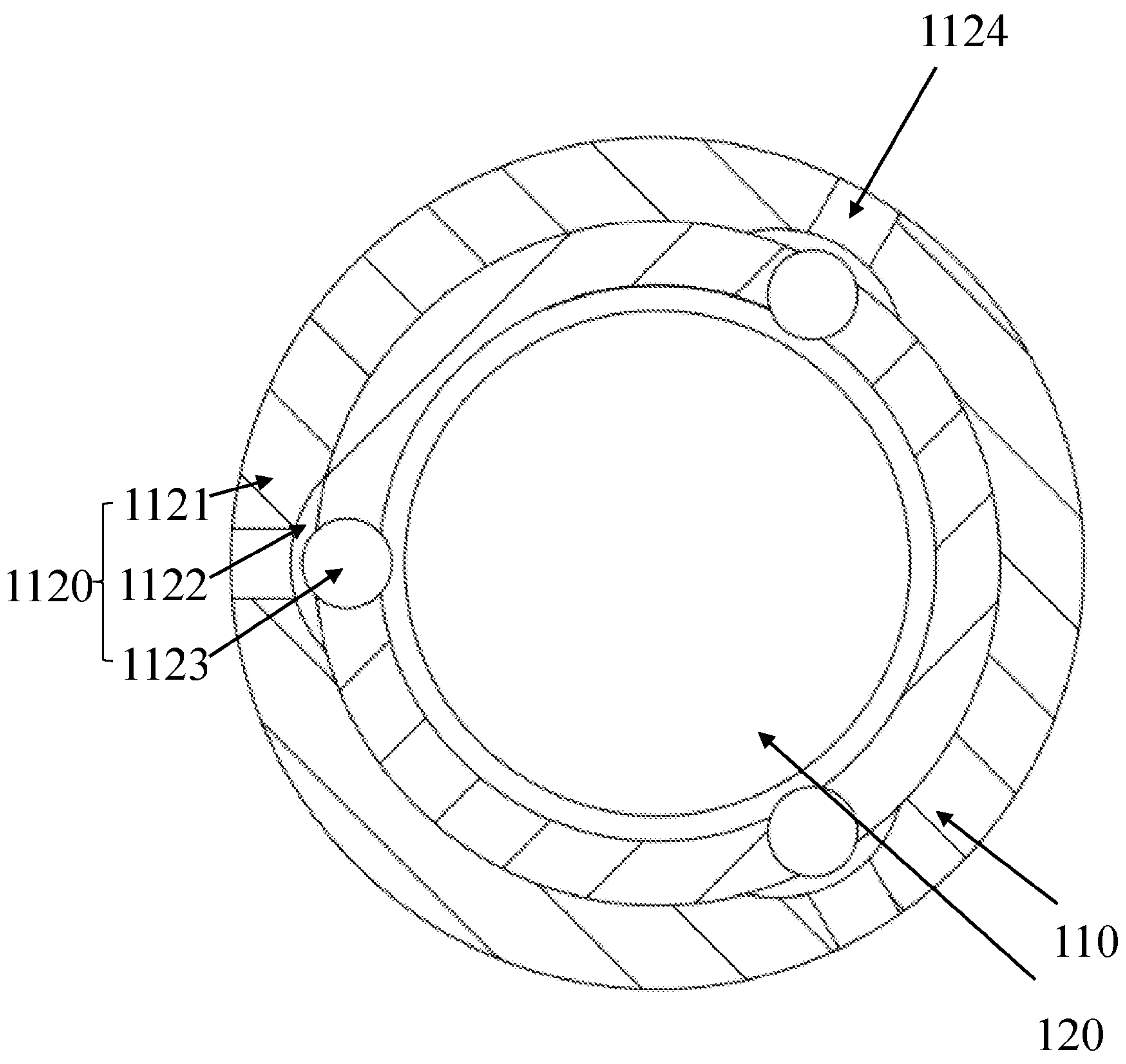
FIG. 9 is a schematic diagram illustrating an exemplary structure of a reversible limiting structure according to some embodiments of the present disclosure.

FIG. 9 is a schematic diagram illustrating an exemplary structure of a reversible limiting structure according to some embodiments of the present disclosure.

In some embodiments, as shown in FIG. 9, the roller 1123 is made of a magnetic material, and the sleeve 1121 may be arranged with a magnetic member 1124 relative to the cavities with varying cross-section 1122.

The magnetic material refers to a material having magnetic characteristic or that can be magnetically adsorbed, such as magnets, iron, or the like. The magnetic member 1124 refers to a structure that is capable of generating a magnetic force, such as at least one of a magnet or an electromagnet, or the like. In some embodiments, the magnetic member 1124 may be configured to attract the roller 1123. During the transition of the reversible limiting structure 1120 from the unlimiting state to the limiting state, the squeeze of the roller 1123 by the cavity with varying cross-section 1122 may overcome an attraction force between the magnetic member 1124 and the roller 1123, thereby gradually pushing the roller 1123 inward along the radial direction of the fixing body 110. During the transition of the reversible limiting structure 1120 from the limiting state to the unlimiting state, a gap between the variable cross-section cavity 1122 and the roller 1123 may formed, marking the e magnetic member 1124 attracting the roller 1123, thereby gradually undoing the pressure of the roller 1123 on the bottle 120.

By using the magnetic member to attract the roller, a plurality of rollers may quickly reset simultaneously, which can facilitate a fast reset of the bottle body and offer the advantage of convenience in use.

Figure 10:
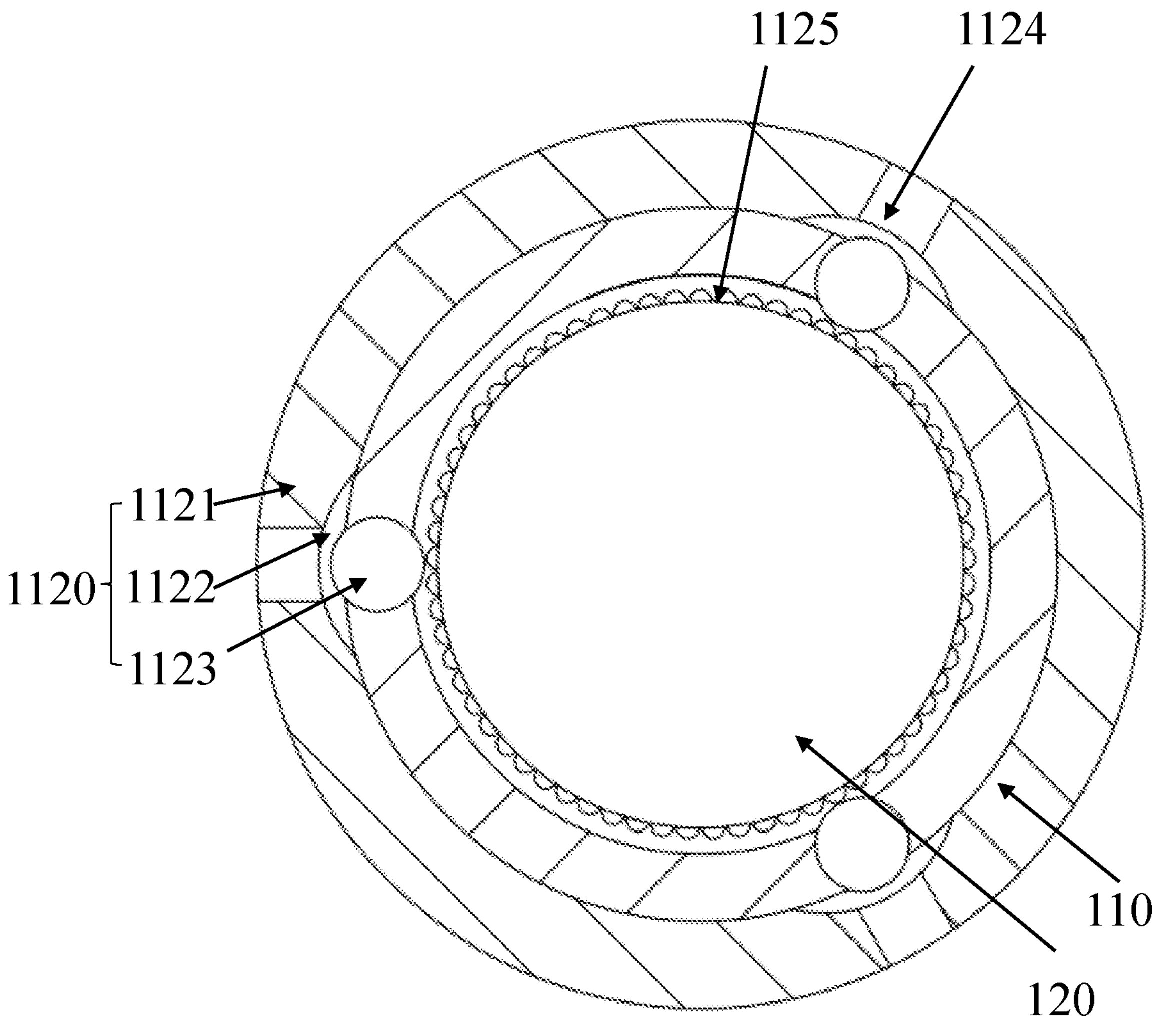
FIG. 10 is a schematic diagram illustrating an exemplary structure of a reversible limiting structure according to some embodiments of the present disclosure.

FIG. 10 is a schematic diagram illustrating an exemplary structure of a reversible limiting structure according to some embodiments of the present disclosure In some embodiments, as shown in FIG. 10, a wrinkled member 1125 may be arranged on an inner side of the fixing body 110.

The wrinkled member 1125 refers to a structure that forms wrinkles on the surface. In some embodiments, the wrinkled member 1125 may be arranged between the roller 1123 and the bottle body 120. In some embodiments, the wrinkled member 1125 may be a cylindrical structure. In some embodiments, a plurality of wrinkled members 1125 may be provided and correspond to the roller 1123. In some embodiments, the wrinkles may be wavy, curved, or the like. In some embodiments, an inner side and an outer side of the wrinkled member 1125 are both formed with pleats. In some embodiments, the wrinkled member 1125 may be an clastic structure. For example, the wrinkled member 1125 may be made of a material such as rubber, silicone, plant fiber, or the like. In some embodiments, the wrinkled member 1125 may be connected with the fixing body 110 such as bonding, or the like.

When the roller squeezes the bottle body, the pressure may be exerted on the bottle body through the wrinkled member, which may change a point contact between the roller and the bottle body to a surface contact between the wrinkled member and the bottle body, thereby reducing a pressure strength on a unit area of the bottle body and preventing the roller from crushing the bottle body. The wrinkles on the surface of the wrinkled member may provide the wrinkled member with a certain deformation capacity, which is also conducive to distributing the pressure from the roller.

Figure 11:
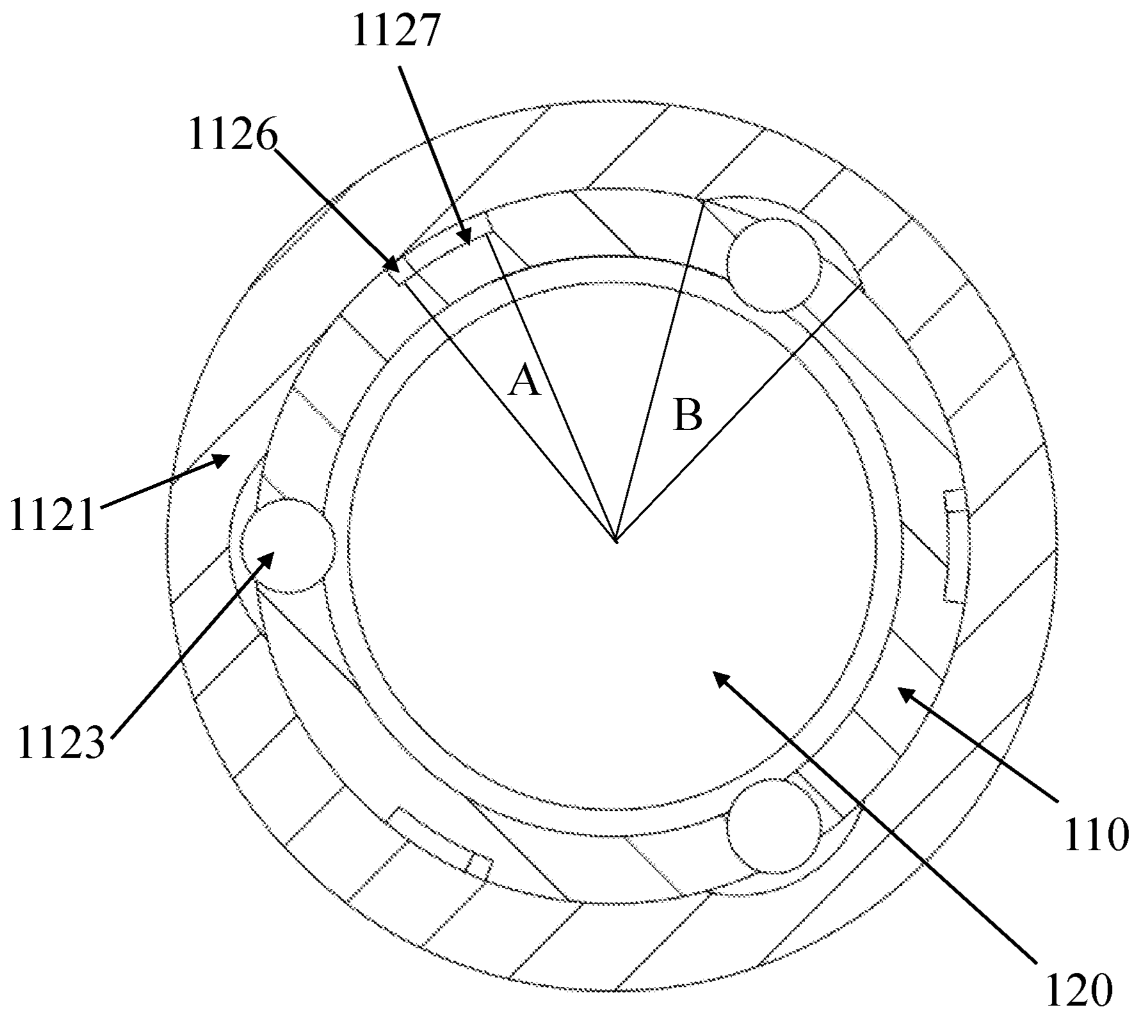
FIG. 11 is a schematic diagram illustrating exemplary positions of a protrusion and a groove according to some embodiments of the present disclosure.

FIG. 11 is a schematic diagram illustrating exemplary positions of a protrusion and a groove according to some embodiments of the present disclosure.

In some embodiments, as shown in FIG. 11, a protrusion 1126 may be arranged on a contact surface (e.g., an end face and/or an inner face of the sleeve 1121) of the sleeve 1121 and the fixing body 110. The protrusion 1126 refers to a structure that protrudes outwardly relative to a surface of the sleeve 1121 (e.g., an end face or an inner face of the sleeve 1121).

In some embodiments, the fixing body 110 may be arranged with a groove 1127 as shown in FIG. 11, and in some embodiments, the protrusion 1126 may be located within the groove 1127. When the reversible limiting structure 1120 switches between the limiting state and the unlimiting state, the protrusion 1126 may slide within the groove 1127. The groove 1127 may limit a range of a movement of the protrusion 1126, thereby limiting a relative rotation range of the fixing body 110 and the sleeve 1121.

In some embodiments, a sliding angle of the protrusion 1126 1126 within groove 1127 is a first included angle such as an angle A in FIG. 11. An included angle formed by the cavity with varying cross-section 1122 relative to the axis of the sleeve 1121 is a second included angle, such as an angle B in FIG. 11. By setting the groove 1127 and the protrusion 1126, a relative rotation range of the fixing body 110 and the sleeve 1121 may be limited. In some embodiments, an angle of the first included angle may be one-half of the second included angle. When the protrusion 1126 moves from one end of the groove 1127 to the other end, the cavity with varying cross-section 1122 may rotate an angle of half of the second included angle, i.e., aligning a center or axis of the roller 1123 from a middle of the cavity with varying cross-section (i.e., a largest radial dimension along the fixed body 110), and rotating to an edge of the cavity with varying cross-section (i.e., a smallest radial dimension along the fixing body 110) and aligning a center or axis of the roller 1123. In some embodiments, the protrusion 1126 may be arranged on the limiting ring 130, and the groove 1127 may be arranged at a corresponding position of the sleeve 1121.

In some embodiments, a scale may be arranged on an outer side of the sleeve 1121 and the fixing body 110. The scale may be read to understand a relative rotation angle of the fixing body 110 and the sleeve 1121.

By using a fit of the protrusion and the groove to limit the relative rotation angle of the fixing body and the sleeve, a control precision can be improved when the fixing body rotates relative to the sleeve.

In some embodiments, as shown in FIG. 6, a baffle 1200 may be arranged at a bottom of the fixing body 110. An exemplary process for installing the sleeve 1121 and the fixing body 110 may include fixing the baffle 1200 on the fixing body 110 after installing the sleeve 1121 and the roller 1123, such as fixing by screwing, pinning, snap-fitting, gluing, or the like. The baffle 1200 may block the sleeve 1121 to complete the installation.

Figure 12:
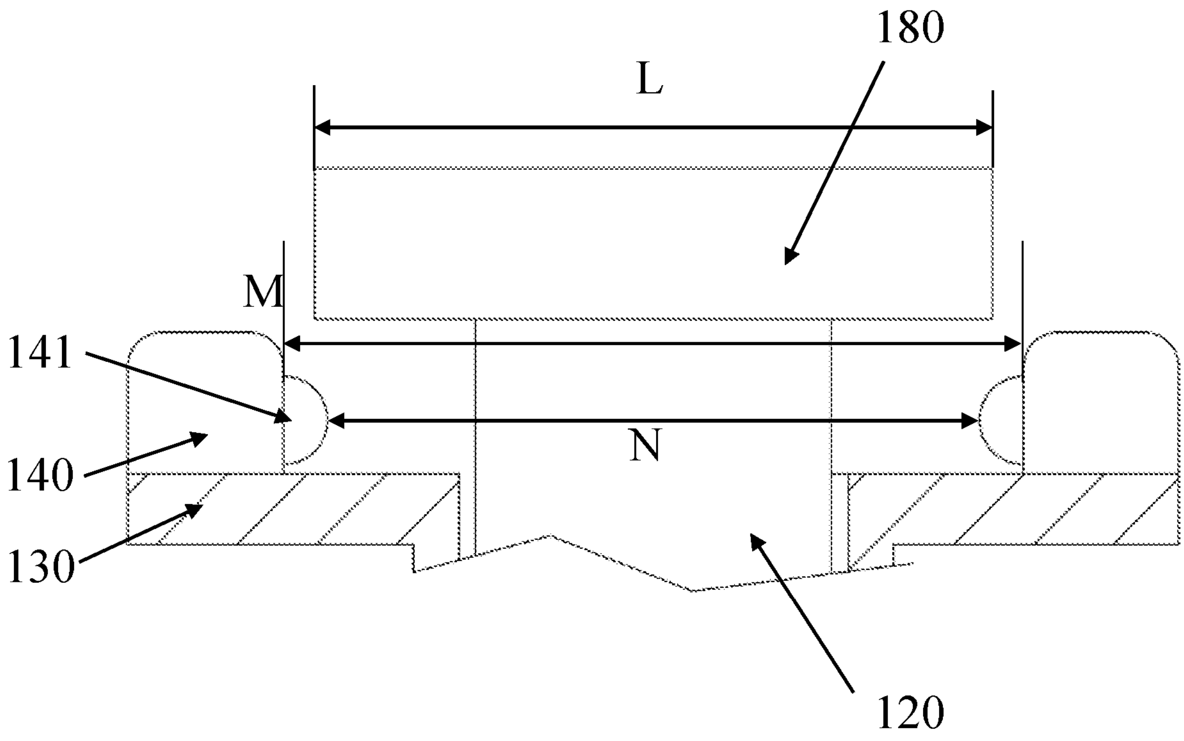
FIG. 12 is a schematic diagram illustrating an exemplary structure of a side limiting component according to some embodiments of the present disclosure.

FIG. 12 is a schematic diagram illustrating an exemplary structure of a side limiting component according to some embodiments of the present disclosure.

Figure 13:
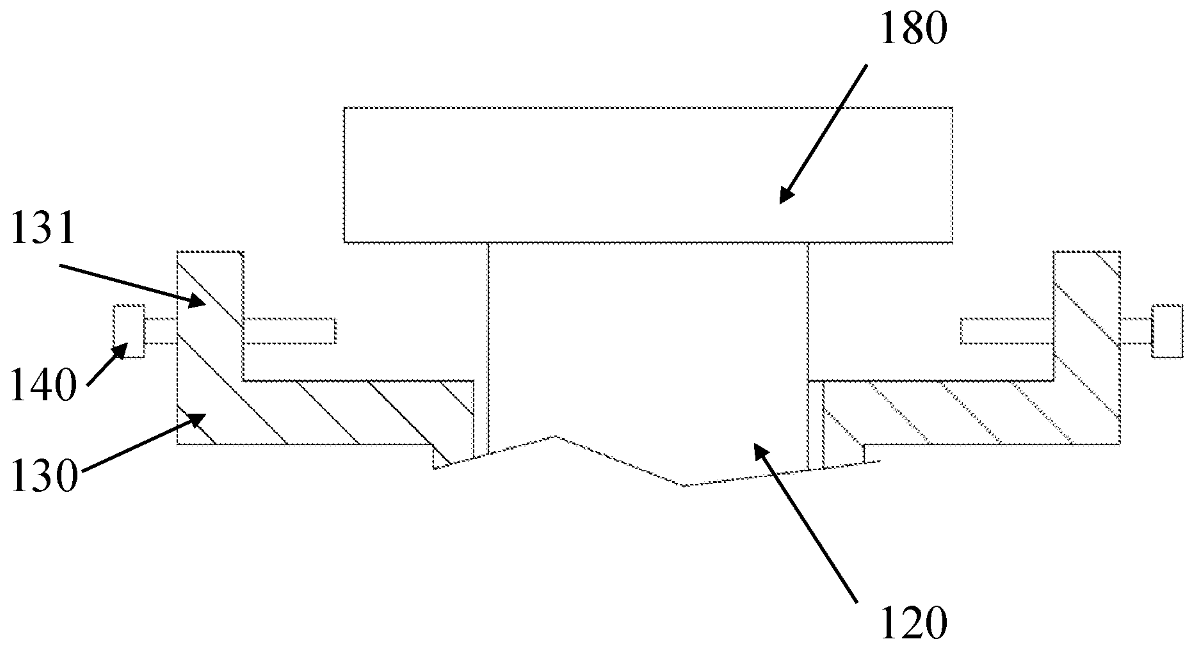
FIG. 13 is a schematic diagram illustrating another exemplary structure of a side limiting component according to some embodiments of the present disclosure.

In some embodiments, each of the side limiting components 140 may be made of an elastic material, such as at least one of rubber, silicone, or the like. In some embodiments, as shown in FIG. 13, a side of the side limiting component 140 near the bottle body 120 is an arc-shaped surface 141, and the arc-shaped surface 141 may not contact the limiting ring 130. In some embodiments, the arc-shaped surface 141 may be in elastic contact with the flange structure 180 of the bottle body 120. In some embodiments, a maximum distance between the outer side of the flange structure 180 (e.g., an outer diameter of the flange structure 180) may be L. A maximum distance between sides of two mirror-symmetrical side limiting component 140 near the bottle body 120 may be M. A minimum distance between the two arc-shaped surfaces 141 may be N, where M>L>N. When the flange structure 180 is placed in place, the outer side of the flange structure 180 may squeeze the arc-shaped surface 141, thereby elastically connecting the arc-shaped surface 141 with the flange structure 180. By ensuring that the arc-shaped surface 141 do not contact the limiting ring 130, a certain gap may be left between the arc-shaped surface 141 and the limiting ring 130, thereby providing a space for an elastic deformation of the arc-shaped surfaces 141.

By providing the arc-shaped surface, the elasticity of the arc-shaped surface may be used to deform the flange structure and apply a compression force, thus improving a strength of the connection between the side limiting component and the flange structure and enhancing a limiting effect of the side limiting components on the flange structure.

FIG. 13 is a schematic diagram illustrating another exemplary structure of a side limiting component according to some embodiments of the present disclosure.

In some embodiments, as shown in FIG. 13, each of the side limiting component 140 may be a screw rod. The limiting ring 130 may be arranged with a flanging 131 and the screw rod may be connected with the flanging 131. The flanging 131 is a protrusion that forms an angle with a side of the limiting ring 130 on at least one side of the limiting ring 130. In some embodiments, the flanging 131 may be arranged on the side of the limiting ring 130 near the guiding cycle 160. In some embodiments, an angle between the flanging 131 and the limiting ring 130 may be 90°. In some embodiments, the screw rod may be connected with the flanging 131 through thread, by rotating the screw rod, the screw rod may move back and forth along the axial direction. In some embodiments, an axis of the screw rod may be parallel to a side of the limiting ring 130 near the guiding cycle 160. After the flange structure 180 is placed in place, the screw rod may be rotated to move the screw rod until abutting with the flange structure 180, thereby using the screw rod to clamp the flange structure 180. In some embodiments, by using two mirror-image symmetric screw rods to simultaneously clamp the flange structure 180, the effectiveness of the screw rods in clamping the flange structure 180 may be increased. In some embodiments, an elastic cushion block may be arranged at an end of the screw rod near the flange structure 180. By using an elastic connection between the clastic cushion block and the flange structure 180, the clamping effect of the screw rod on the flange structure may be enhanced, and the possibility of the screw rod crushing the flange structure 180 may be avoided. The clastic cushion block may be made of rubber, silicone, or the like.

By clamping the flange structure with the screw rod, a position of the screw rod may be adjusted to accommodate different sizes of flange structures, thereby expanding the applicability of the anti-loosening fixing structure.

Figure 14:
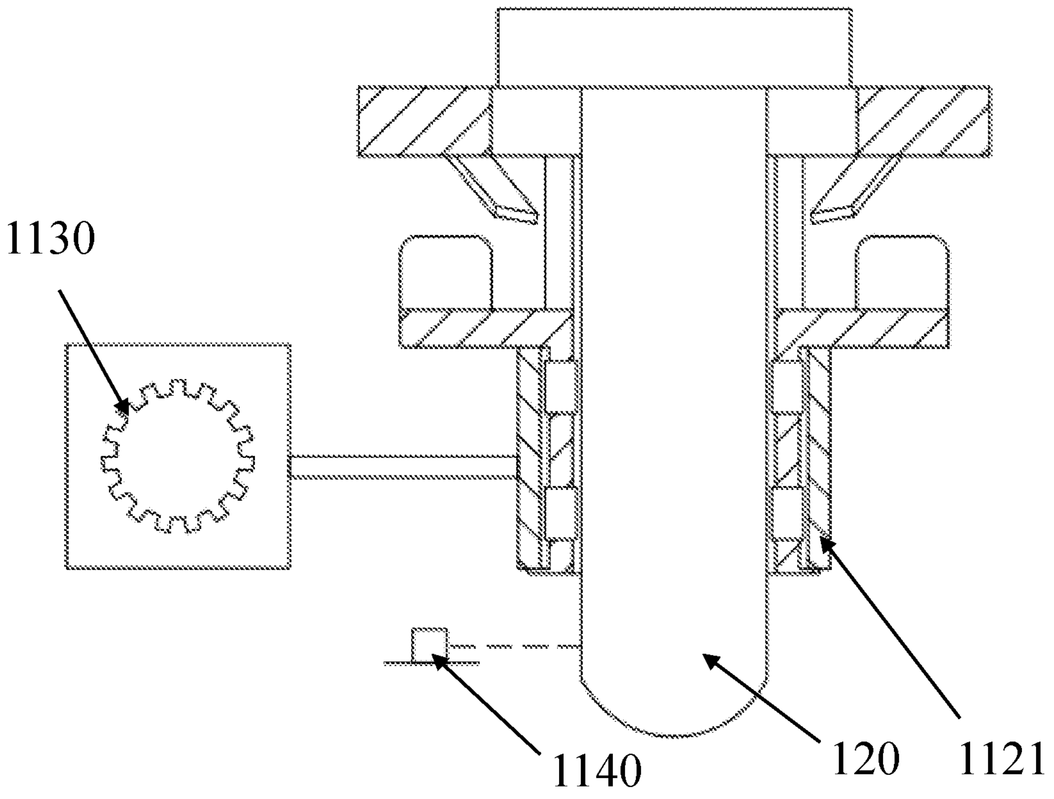
FIG. 14 is a schematic diagram illustrating an exemplary structure of an anti-loosening fixing structure according to some embodiments of the present disclosure.

FIG. 14 is a schematic diagram illustrating an exemplary structure of an anti-loosening fixing structure according to some embodiments of the present disclosure.

In some embodiments, as shown in FIG. 14, the anti-loosening fixing structure 100 may further include a drive device 1130, a processor, and a range sensor 1140. The drive device 1130 and the range sensor 1140 may communicate with the processor.

The drive device 1130 refers to a device capable of providing a driving force to move and/or rotate other structures, such as gears, shafts, or the like. For example, the drive device 1130 may be a motor, a hydraulic cylinder, a cylinder, or the like. In some embodiments, the drive device 1130 may be connected with the sleeve 1121 for transmission. In some embodiments, the drive device 1130 may drive a rotation of the sleeve 1121. For example, an outer side of the sleeve 1121 may be arranged with a sleeve gear coaxial with the sleeve, and the drive device 1130 may drive a rotation of the sleeve gear via a transmission structure (e.g., a gear, a reduction gearbox, etc.), thereby driving the rotation of the sleeve.

The range sensor 1140 refers to a sensor configured to detect a distance. In some embodiments, the range sensor 1140 may be configured to measure a diameter of the bottle body 120.

The processor may be configured to collect, analyze, and process data, and generate a control instruction based on the data, and the processor may send the control instruction to an actuator (e.g., the drive device 1130, the range sensor 1140, etc.) to make the actuator perform corresponding functions and/or actions. In some embodiments, the processor may send the control instruction to the drive device 1130 to enable the drive device 1130 to perform at least one of the functions of starting up, shutting down, outputting a torque to drive the sleeve 1121 to rotate, changing the output torque, and other functions. The processor may send the control instruction to the range sensor 1140 to enable the range sensor 1140 to perform at least one of the functions of starting up, shutting down, measuring the diameter of the bottle body 120, or the like. In some embodiments, the processor may collect data generated or detected by the drive device 1130 and the range sensor 1140.

By using a processor to control the drive motor to rotate the sleeve, a degree of automation and work precision of the anti-loosening fixing structure may be improved.

In some embodiments, the processor may be configured to: obtain current data of the drive device 1130, and determine whether the anti-loosening fixing structure 100 is fixed in place with the bottle body 120 based on the current data.

The current data refers to data relating to the current generated during the operation of the drive device 1130. In some embodiments, the current data may include at least one of the current value and a current variation magnitude. In some embodiments, the drive device 1130 may collect the current data according to a pre-determined rule. For example, the drive device 1130 may collect the current data at a pre-determined time point or at a pre-determined time interval.

The current value refers to a numerical value that reflects a magnitude of the current, such as 1A, 5A, or the like. The current variation magnitude refers to data that reflects a change of the current value. In some embodiments, the current variation magnitude may be a ratio of a current difference between two adjacent time point to a time difference between the two adjacent time points. For example, the current variation magnitude may be equal to a difference between a current at a second time point and a current at a first time point divided by a difference between the second time point and the first time point.

In some embodiments, the processor may determine, based on the current variation magnitude, whether the anti-loosening fixing structure 100 is fixed in place with the bottle body 120. For example, when the drive device 1130 is in operation and the current is increasing, the torque output from the drive device 1130 may gradually increase. When the torque reaches a maximum value, it may be determined that the anti-loosening fixing structure 100 is fixed in place with the bottle body 120.

The processor may determine whether the bottle body is fixed in place based on the current change of the drive device, thereby achieving automated judgment and improving an automation degree of the anti-loosening fixing structure, increasing the accuracy and efficiency of the judgment, and facilitating the improvement of automated control accuracy.

In some embodiments, the processor may be configured to: obtain the diameter of the bottle body 120 and transmit a first control instruction of the drive device 1130 based on the diameter of the bottle body 120.

The first control instruction refers to an instruction for the processor 1150 to control the drive device 1130, so as to drive the sleeve 1121 to rotate at a first rotation angle. The first rotation angle refers to a center angle corresponding to the rotation of the sleeve 1121. More descriptions of the first rotation angle may be found in following descriptions.

In some embodiments, the sleeve 1121 may be rotated with the roller 1123 starting from a middle of the cavity with varying cross-section 1122 (i.e., a maximum dimension along the radial direction of the fixing body 110) to an edge of the cavity with varying cross-section 1122 (i.e., a minimum dimension along the radial direction of the fixing body 110). At this time, the roller 1123 exerts a maximum pressure on the bottle body 120. To prevent the roller 1123 from crushing the fragile bottle body 120 (e.g., a glass bottle body), the sleeve 1121 does not necessarily have to rotate to a point where the roller 1123 is located at the edge of the cavity with varying cross-section 1122.

In some embodiments, the processor may obtain the diameter of the bottle body 120 based on the range sensor and determine the first rotation angle based on the diameter of the bottle body 120 through various feasible processes. For example, the processor may establish a predetermined relationship table based on the diameter of the bottle body 120 and the first rotation angle in the historical data, and determine the first rotation angle by looking up the table.

Figure 15:
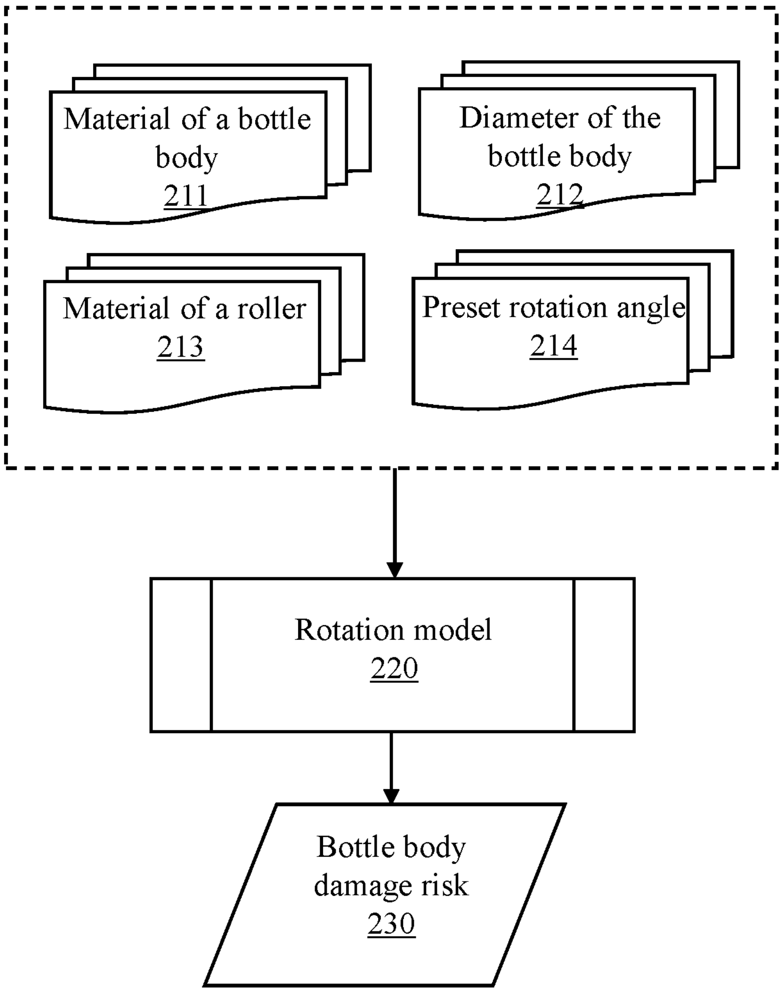
FIG. 15 is a schematic diagram illustrating an exemplary structure of a rotating model according to some embodiments of the present disclosure.

FIG. 15 is a schematic diagram illustrating an exemplary structure of a rotating model according to some embodiments of the present disclosure.

In some embodiments, as shown in FIG. 15, the processor may determine, based on a material 211 of the bottle body, a diameter 212 of the bottle body, a material 213 of the roller, and a preset rotation angle 214, a bottle body damage risk 230 by a rotation model 220, and determine the first rotation angle 240 based on the bottle body damage risk 230.

The rotation model 220 refers to a model for determining the bottle body damage risk 230. In some embodiments, the rotation model may be a machine learning model, such as a Neural Networks (NNs), or the like.

In some embodiments, inputs to the rotation model 220 may include the material 211 of the bottle body, the diameter 212 of the bottle body, the material 213 of the roller, and the preset rotation angle 214, and the output may be the bottle body damage risk 230.

The material 211 of the bottle body refers to a material used to make the bottle body. The material 213 of the roller refers to a material used to make the roller. In some embodiments, the processor may include an input device, such as a touch screen, a keyboard, or the like, and the material 211 of the bottle body and the material 213 of the roller may be obtained based on at least one of the vendors and historical data, and input to the processor manually via the input device.

The preset rotation angle 214 refers to a preset angle at which the drive device 1130 drives the sleeve 1121 to rotate. The preset rotation angle 214 may fall within a range of the first included angle. In some embodiments, the preset rotation angle 214 may be a specific angle or a percentage such as a rotation of 20°, or 80% representing that the rotation angle is a value of a first included angle *80%.

The bottle body damage risk 230 refers to a probability that the bottle body 120 is damaged by the roller 1123. In some embodiments, the bottle body damage risk 230 may be expressed as a percentage, and the greater the percentage, the higher the possibility of bottle body 120 damage.

In some embodiments, the rotation model may be trained using multiple first training samples with a first label. The multiple first training samples with the first label may be input into an initial rotation model. A loss function may be constructed based on the first label and a result of the initial rotation model. The parameters of the initial rotation model may be iteratively updated based on the loss function. The model training may be completed when the loss function of the initial rotation model satisfies a predetermined condition, resulting in a trained rotation model. The predetermined condition may include convergence of the loss function, reaching a threshold count of iterations, or the like.

In some embodiments, the first training sample may include a sample material of the bottle body, a sample diameter of the bottle body, a sample material of the roller, and a sample preset rotation angle. In some embodiments, the first label may indicate whether or not the sample is damaged. The first label may include 1 and 0, where I represents damage, 0 represents not damage. In some embodiments, the first label may be determined based on actual occurrences of damage during the historical actual occurrences or simulated experiments of a fixing process of the bottle body under a condition of the first training sample, where a label representing the actual occurrence of damage is 1, a label representing the occurrence of no damage is 0.

In some embodiments, a training of the rotation model may be performed on a remote server.

In some embodiments, the processor may select a preset rotation angle corresponding to a bottle body damage risk that is less than a preset risk threshold, and the preset rotation angle that is the largest among the preset rotation angles may be determined as the first rotation angle. The preset risk threshold refers to a preset risk value. For example, the preset risk threshold may be a 50% risk of damage. In some embodiments, the preset risk threshold may be obtained based on at least one of experience, historical data, or the like.

The bottle bodies with different diameters and/or different materials may withstand different maximum pressures. If a consistent rotation angle is uniformly set, there is a greater risk of damage to bottle bodies that are more fragile (e.g., made of more brittle materials, etc.). By using the rotation model, based on parameters such as the material of the bottle body, the diameter of the bottle body, and the material of the rollers, it is possible to quickly determine a reasonable rotation angle that avoids damaging the bottle body and improve the applicability of the anti-loosening fixing structure.

In some embodiments, the anti-loosening fixing structure 100 may further include a sensing device (not shown in the figures). The sensing device may be configured to detect whether the bottle body 120 is placed in place, and the sensing device may communicate with the processor 1150.

The sensing device is a device that may sense the measured information and transform it into an electrical signal or other desired form of information for output according to a certain law. For example, the sensing device may include a sensor, or the like. In some embodiments, the sensing device may include at least one of a photoelectric sensor or a pressure sensor. The photoelectric sensor may be configured to detect a distance between the bottle body 120 and the photoelectric sensor to determine whether the bottle body 120 is placed in place. For example, if the photoelectric sensor detects that the distance between the bottle body 120 and the photoelectric sensor satisfies a preset condition to determined that the bottle body 120 is placed in place. The preset condition may be that the distance between the bottle body 120 and the photoelectric sensor reaches a preset value, such as 0, or the distance between the bottle body 120 and the photoelectric sensor decreases from a large value to a value that remains unchanged. The pressure sensor may be configured to detect the pressure exerted by the bottle body 120 on the pressure sensor to determine whether the bottle body 120 is placed in place. For example, if the pressure sensor detects that the pressure meets a set pressure threshold, it may be determined that the bottle body 120 is placed in place.

In some embodiments, the processor may send a second control instruction to the drive device based on the sensing data. The sensing data refers to relevant data output by the sensing device. In some embodiments, the sensing data may include at least one of the bottle body 120 being placed in place, the bottle body 120 not being placed in place, or the like. In some embodiments, in response to determining that the bottle body 120 is placed in place, the processor may send the second control instruction to the drive device.

The second control instruction refers to an instruction in which the processor 1150 control the drive device 1130 to operate according to a drive power and drive the sleeve 1121 to rotate according to the second rotation angel. The second rotation angle is similar to the first rotation angle and may be determined in the same manner as the first rotation angle, more descriptions may be found in related descriptions of the first rotation angle.

The drive power refers to a relevant parameter during the operation of the drive device 1130. In some embodiments, when the drive device 1130 operates at different drive powers, different torques may be output, thus driving the sleeve 1121 to rotate at different speeds. In some embodiments, the drive power may be obtained based on empirical or historical data. For example, the processor may select historical drive power corresponding to the second rotation angle from the historical data as a target drive power.

In some embodiments, the drive power may be inversely correlated to the bottle body damage risk. For example, the lower the bottle body damage risk, the greater the drive power may be. In some embodiments, the drive power may be calculated by the processor based on a predetermined algorithm. For example, the drive power may be equal to a product of a baseline drive power, a difference value between 1 and the bottle body damage risk, and a bottle body material factor. The baseline drive power may be a preset value. For example, the baseline drive power may be an average value of the drive powers in the historical data. The bottle body material factor may be a preset value. In some embodiments, the bottle body material factor may be obtained based on at least one of experience, historical data, lookup tables, or the like.

By controlling the drive power of the drive device, it is possible to control the rotation speed of the sleeve, so as to avoid the sleeve rotating at an excessively large angle due to inertia or control lag, which may result in the roller crushing the bottle body. Since bottle bodies made of different materials have different tolerance values for the squeezing pressure endured during rotation, the preset algorithm may reasonably determine the drive power and rotation speed. Thus, when it is detected that the tolerance value of the bottle body pressure is reached, the algorithm may determine the appropriate drive power and rotation speed to timely stop the sleeve and avoid damaging the bottle body.

The basic concepts have been described above, obviously, to those skilled in the art, the above detailed disclosure is intended as an example only and does not constitute a limitation of the present disclosure. Although there is no clear explanation here, those skilled in the art may make various modifications, improvements, and modifications of present disclosure. This type of modification, improvement, and corrections are recommended in present disclosure, so the modification, improvement, and the amendment remain in the spirit and scope of the exemplary embodiment of the present disclosure.

At the same time, present disclosure uses specific words to describe the embodiments of the present disclosure. As "one embodiment", "an embodiment", and/or "some embodiments" means a certain feature, structure, or characteristic of at least one embodiment of the present disclosure.

Therefore, it is emphasized and should be appreciated that two or more references to "an embodiment" or "one embodiment" or "an alternative embodiment" in various parts of present disclosure are not necessarily all referring to the same embodiment. Further, certain features, structures, or features of one or more embodiments of the present disclosure may be combined.

Moreover, unless the claims are clearly stated, the sequence of the present disclosure, the use of the digital letters, or the use of other names is not configured to define the order of the present disclosure processes and methods. Although some examples of the disclosure currently considered useful in the present disclosure are discussed in the above disclosure, it should be understood that the details will only be described, and the appended claims are not limited to the disclosure embodiments. The requirements are designed to cover all modifications and equivalents combined with the substance and range of the present disclosure. For example, although the implementation of various components described above may be embodied in a hardware device, it may also be implemented as a software only solution, e.g., an installation on an existing server or mobile device.

Similarly, it should be noted that in order to simplify the expression disclosed in the present disclosure and help the understanding of one or more embodiments, in the previous description of the embodiments of the present disclosure, a variety of features are sometimes combined into one embodiment, drawings or description thereof. However, this disclosure method does not mean that the characteristics required by the object of the present disclosure are more than the characteristics mentioned in the claims. Rather, claimed subject matter may lie in less than all features of a single foregoing disclosed embodiment.

In some embodiments, numbers expressing quantities of ingredients, properties, and so forth, configured to describe and claim certain embodiments of the application are to be understood as being modified in some instances by the term "about," "approximate," or "substantially". Unless otherwise stated, "approximately", "approximately" or "substantially" indicates that the number is allowed to vary by +20%. Accordingly, in some embodiments, the numerical parameters used in the specification and claims are approximate values, and the approximate values may be changed according to characteristics required by individual embodiments. In some embodiments, the numerical parameters should be construed in light of the number of reported significant digits and by applying ordinary rounding techniques. Although the numerical domains and parameters used in the present disclosure are configured to confirm its range breadth, in the specific embodiment, the settings of such values are as accurately as possible within the feasible range.

For each patent, patent application, patent application publication and other materials referenced by the present disclosure, such as articles, books, instructions, publications, documentation, etc., hereby incorporated herein by reference. Except for the application history documents that are inconsistent with or conflict with the contents of the present disclosure, and the documents that limit the widest range of claims in the present disclosure (currently or later attached to the present disclosure). It should be noted that if a description, definition, and/or terms in the subsequent material of the present disclosure are inconsistent or conflicted with the content described in the present disclosure, the use of description, definition, and/or terms in this manual shall prevail.

Finally, it should be understood that the embodiments described herein are only configured to illustrate the principles of the embodiments of the present disclosure. Other deformations may also belong to the scope of the present disclosure. Thus, as an example, not limited, the alternative configuration of the present disclosure embodiment may be consistent with the teachings of the present disclosure. Accordingly, the embodiments of the present disclosure are not limited to the embodiments of the present disclosure clearly described and described.

What is claimed is:

1. An anti-loosening fixing structure for a bottle body of a flange bottle, comprising a fixing body, wherein
- the fixing body has an internal cavity extending along an axial direction, and the internal cavity is configured to receive the bottle body,
- the top end of the fixing body is arranged with a limiting ring,
- the limiting ring is arranged with side limiting components that are arranged in a mirror distribution,
- a storage space configured for installing an upper end of the bottle body is provided between the side limiting components,
- an elastic support structure is arranged in the storage space,
- the upper end of the fixing body is arranged with a guiding cycle,
- the guiding cycle is arranged with upper end limiting components that are arranged in the mirror distribution,
- the upper end limiting components are configured to contact a flange structure arranged at the upper end of the bottle body, wherein
  - a lower end of the fixing body is arranged with a reversible limiting structure, wherein the reversible limiting structure comprises a sleeve and a roller;
  - the sleeve is arranged at an outer side of the lower end of the fixing body;
  - the roller is arranged on the fixing body;
  - the roller is located between the fixing body and the sleeve;
  - an inner side of the sleeve is arranged with one or more cavities with varying cross-section; and
  - at least a portion of the roller is arranged in the one or more cavities with varying cross-section.

2. The anti-loosening fixing structure for the bottle body of the flange bottle of claim 1, wherein each of the side limiting components is an elastic block.

3. The anti-loosening fixing structure for the bottle body of the flange bottle of claim 2, wherein each of the side limiting components is a rectangular sheet, a top of the rectangular sheet is arranged with an arc chamfer.

4. The anti-loosening fixing structure for the bottle body of the flange bottle of claim 1, wherein the elastic support structure is an elastic support arm, the elastic support arm includes an elastic cross-piece, the elastic cross-piece is vertically arranged with an arm body, and an upper end of the arm body is arranged with a support block.

5. The anti-loosening fixing structure for the bottle body of the flange bottle of claim 1, wherein each of the upper end limiting components is an oblique limiting valve, a bottom of the oblique limiting valve is arranged with an oblique slope.

6. The anti-loosening fixing structure for the bottle body of the flange bottle of claim 1, wherein the flange structure is a circular flange.

7. The anti-loosening fixing structure for the bottle body of the flange bottle of claim 1, wherein the flange structure is a notched flange.

8. The anti-loosening fixing structure for the bottle body of the flange bottle of claim 1, wherein a projection of each of the cavities with varying cross-section along an axis direction of the fixing body includes a plurality of oblique lines and/or at least one arc.

9. The anti-loosening fixing structure for the bottle body of the flange bottle of claim 1, wherein a count of the one or more cavities with varying cross-section is two or more, and the two or more cavities are distributed around the axis direction of the fixing body.

10. The anti-loosening fixing structure for the bottle body of the flange bottle of claim 1, wherein the roller is made of elastic material.

11. The anti-loosening fixing structure for the bottle body of the flange bottle of claim 1, wherein the roller is made of magnetic material, a position of the sleeve relative to each of the one or more cavities is provided with a magnetic member.

12. The anti-loosening fixing structure for the bottle body of the flange bottle of claim 11, wherein an inner side of the fixing body is arranged with an elastic wrinkled member.

13. The anti-loosening fixing structure for the bottle body of the flange bottle of claim 1, wherein a contact surface of the sleeve and the fixing body is provided with a protrusion, the fixing body is provided with a groove, and the protrusion is located in the groove.

14. The anti-loosening fixing structure for the bottle body of the flange bottle of claim 1, wherein a side limiting component of the side limiting components is made of elastic material; and a side surface of each of the side limiting components closest to the bottle body is an arc-shaped surface.

15. The anti-loosening fixing structure for the bottle body of the flange bottle of claim 1, wherein a side limiting component of the side limiting components is a screw rod; the limiting ring is arranged with a flanging, and the screw rod is connected with the flanging.

16. The anti-loosening fixing structure for the bottle body of the flange bottle of claim 1, wherein
- the anti-loosening fixing structure further includes a drive device, a processor, and a range sensor,
- the drive device and the range sensor communicate with the processor;
- the drive device is connected with the sleeve in a transmission way; and
- the range sensor is configured to measure a diameter of the bottle body.

17. The anti-loosening fixing structure for the bottle body of the flange bottle of claim 16, wherein the processor is configured to:
- obtain current data of the drive device; and
- determine whether the anti-loosening fixing structure is fixed in place with the bottle body based on the current data.

18. The anti-loosening fixing structure for the bottle body of the flange bottle of claim 16, wherein the processor is configured to:
- obtain the diameter of the bottle body; and
- transmit a first control instruction of the drive device based on the diameter of the bottle body.

19. The anti-loosening fixing structure for the bottle body of the flange bottle of claim 16, wherein
- the anti-loosening fixing structure further includes a sensing device;
- the sensing device is configured to detect whether the bottle body is placed in place;
- the sensing device communicates with the processor;
- the processor is configured to obtain sensing data of the drive device, and transmit a second control instruction of the drive device based on the sensing data.

* * * * *